(12) United States Patent
Hur et al.

(10) Patent No.: US 8,600,002 B2
(45) Date of Patent: Dec. 3, 2013

(54) DEVICE AND METHOD FOR THE AUTOMATIC COUNTING OF MEDICAL GAUZE

(76) Inventors: Gham Hur, Gyeonggi-do (KR); Kim Jong Hyo, Seoul (KR)

( * ) Notice: Subject to any disclaimer, the term of this patent is extended or adjusted under 35 U.S.C. 154(b) by 315 days.

(21) Appl. No.: 13/029,360

(22) Filed: Feb. 17, 2011

(65) Prior Publication Data

US 2011/0200173 A1 Aug. 18, 2011

(30) Foreign Application Priority Data

Feb. 18, 2010 (KR) .................. 10-2010-0014548

(51) Int. Cl.
*G01N 23/083* (2006.01)
(52) U.S. Cl.
USPC ......... 378/57; 378/4; 378/21; 378/56; 378/62
(58) Field of Classification Search
USPC ................. 378/4, 19, 21, 57, 62, 56, 210
See application file for complete search history.

(56) References Cited

U.S. PATENT DOCUMENTS

| | | | |
|---|---|---|---|
| 3,948,390 A | 4/1976 | Ferreri | |
| 4,136,778 A * | 1/1979 | Wortman et al. | 378/45 |
| 4,354,490 A | 10/1982 | Rogers | |
| 4,605,847 A * | 8/1986 | Schittko et al. | 235/471 |
| 4,784,267 A | 11/1988 | Gessler et al. | |
| 4,832,198 A | 5/1989 | Alikhan | |
| 4,897,859 A * | 1/1990 | Tsukamoto et al. | 377/6 |
| 5,629,498 A | 5/1997 | Pollock et al. | |
| 5,658,077 A | 8/1997 | Hoftman | |
| 7,465,847 B2 | 12/2008 | Fabian | |
| 8,009,799 B2 * | 8/2011 | Doyle et al. | 378/56 |
| 2005/0049563 A1 | 3/2005 | Fabian | |
| 2007/0125392 A1 * | 6/2007 | Olson et al. | 128/899 |
| 2011/0200173 A1 * | 8/2011 | Hur | 378/98.5 |

* cited by examiner

*Primary Examiner* — Thomas R Artman
(74) *Attorney, Agent, or Firm* — Swanson & Bratschun, LLC

(57) ABSTRACT

Provided is a device and method for the automatic counting of medical gauze, which can automatically count the number of medical gauzes used for absorbing blood and other body fluids generated during surgical operations. This device includes a container, which collects the gauze containing radiopaque markers; a support, which supports the container; a radiographic unit, which radiographs the container at various angles using X-ray; a controller, which receives radiographic information from the container and counts the total number of markers in the container using radiographic information; and a display, which operates the system and displays the number of markers calculated by the controller.

19 Claims, 4 Drawing Sheets

DEVICE AND METHOD FOR THE AUTOMATIC COUNTING OF MEDICAL GAUZE

CROSS-REFERENCE(S) TO RELATED APPLICATIONS

The present invention claims priority of Korean Patent Application No. 10-2010-0014548, filed on Feb. 18, 2010, which is incorporated herein by reference.

BACKGROUND OF THE INVENTION

1. Field of the Invention

The present invention relates to a device and method for the automatic counting of medical gauze—more specifically, to a device and method which can automatically count medical gauze used for absorbing blood and other body fluids generated during surgical operations.

2. Description of Related Art

Blood and other body fluids generated during surgical operations should be removed frequently. Typically, blood and other body fluids are removed using medical gauze; thus, medical gauze is absolutely necessary for surgical operations.

Medical gauze used in surgical operations must be removed from the body without fail. However, there are frequently occasions when medical gauze is accidentally left in the body. In this case, the patient is forced to undergo an unnecessary operation to remove the gauze and as a result, the surgeon and hospital are often involved in lawsuits for medical negligence. Therefore, there have been many attempts at creating methods to prevent medical gauze from being left in the body.

As part of such efforts, the IFPN (International Federation of Perioperative Nurses) declared in its 2006 guidelines that the perioperative nurses and circulating nurses should collect and count medical gauze in multiples of five and record such counts before, during, and after each surgical operation. In medical circles, gauze is currently hand-counted based on the IFPN's guidelines. However, counting the used medical gauze manually creates numerous potential problems. For example, the person counting the gauze is exposed to risk of infection, such as AIDS and hepatitis, while handling the contaminated gauze, and/or the count may be not performed accurately due to human error.

In order to solve such problems, various techniques—for example, U.S. Pat. Nos. 3,948,390, 4,354,490, 4,784,267, 4,832,198 and 5,658,077—have been suggested to attempt to provide a system in which the gauze is arranged in such a way as to be easily counted or seen. According to these techniques, accuracy in counting the gauze may be increased, but since the counting is still performed by hand, such techniques are not comprehensive solutions to the aforementioned problems.

Further, U.S. Pat. No. 5,629,498 suggests an apparatus for counting the gauze that involves dropping the gauze into the apparatus one by one. However, since the insertion of the gauze is still performed manually, the apparatus does not eliminate the potential for human error.

Finally, in U.S. Pat. No. 7,465,847 and U.S. Patent Publication No. 20050049563, various other gauze detection techniques are discussed. However, these techniques are simply to detect whether medical gauze remains in the body, and do not include techniques to count the gauze through an automated process.

SUMMARY OF THE INVENTION

The goal of the present invention is to provide a device and method for automatically counting medical gauze, eliminating the potential for human error, unnecessary medical procedures to remove gauze mistakenly left in the body, and costly legal proceedings stemming from such errors.

In order to achieve this goal, the present invention provides a device for counting medical gauze automatically. This device includes gauze with embedded radiopaque markers; a container in which to collect such gauze; a tray for the container; a radiographic unit, which radiographs the container at various angles using X-ray; a controller, which receives radiographs of the container from the radiographic unit and counts the markers in the container using the radiographs; and a display, which receives and displays the number of the markers calculated by the controller.

Further, the present invention also provides a method for counting medical gauze automatically. This method involves obtaining radiographs of the abovementioned receiving container; calculating the number of markers in the container using radiographs of the container taken at various angles; and displaying the total calculated number of markers.

DETAILED DESCRIPTION OF MAIN ELEMENTS

Figure 1:
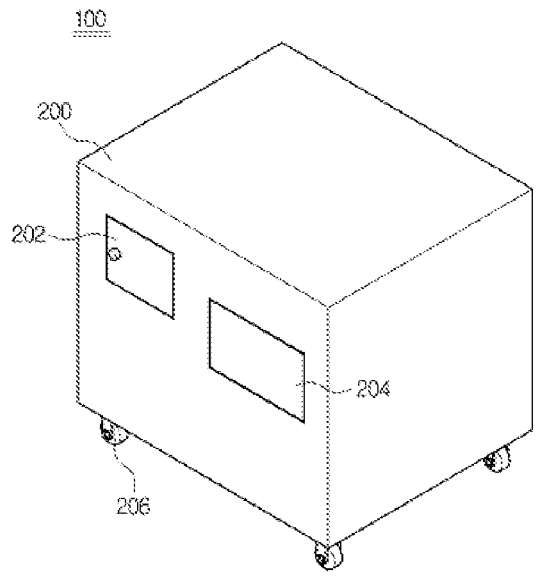
FIG. 1 is a perspective view of the cabinet of the device for automatically counting medical gauze according to the present invention.

10: gauze
12: marker
14: cloth
100: device for automatically counting medical gauze
200: cabinet
204: display
300: container
308: dividing plate
310: holes
320: tray
402: X-ray tube
404: detector
408: arm
500: calibration unit
502: frame
504: background material
506: calibration marker
600: generator
700: controller

DESCRIPTION OF SPECIFIC EMBODIMENTS

The following descriptions, along with the accompanying diagrams, will comprehensively illustrate the features and advantages of this invention. The terms used in the descriptions below are not limited to their typical or dictionary definitions.

Figure 2:
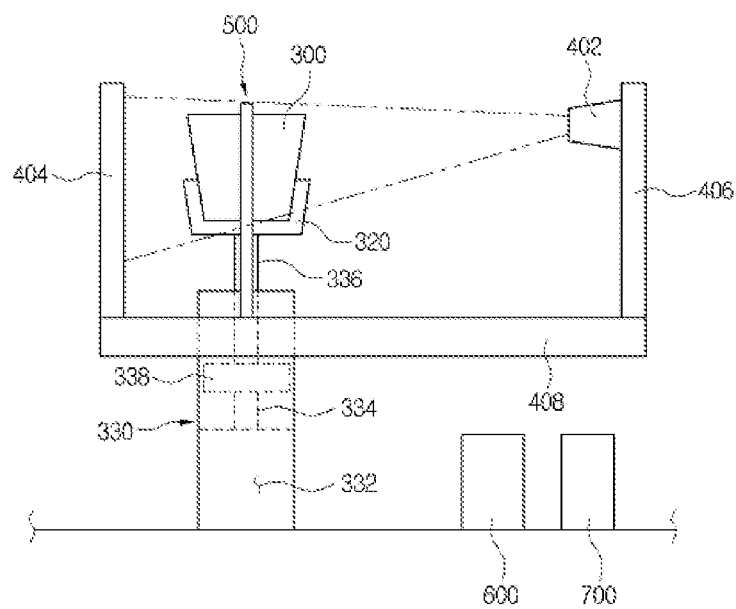
FIG. 2 is a schematic drawing of the components of the device when the cabinet shown in FIG. 1 is removed.
Figure 3:
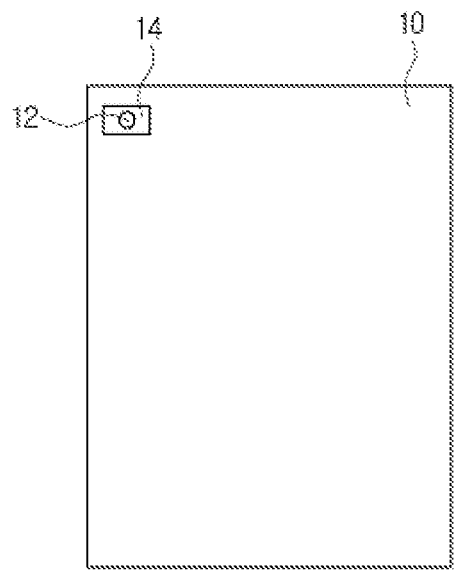
FIG. 3 is a piece of gauze with the embedded radiopaque marker (upper right-hand corner).

As shown in FIGS. 1 and 2, the device 100 for automatically counting medical gauze according to the present invention includes a cabinet 200, a container 300, a tray 320, a radiographic unit, a calibration unit 500, a generator 600, a controller 700, and a display 204.

The cabinet 200, which is composed of X-ray shielding material, receives the container 300, the tray 320, the radiographic unit, the calibration unit 500, the generator 600, and the controller 700. The cabinet 200 is opened and closed with a door 202 such that the container 300 can be installed in and removed from the cabinet 200. The cabinet has a display 204, which is configured such that the user can visually confirm contents and input information. Casters 206 are attached to the bottom of the cabinet 200 for easy mobility.

The container 300, consisting of radiolucent material, receives the gauze 10, embedded with radiopaque markers 12. Fore easier storage in small spaces, the diameter of the container 300 gradually increases from the lower end of the container 300 to the upper end (FIG. 4).

Figure 4:
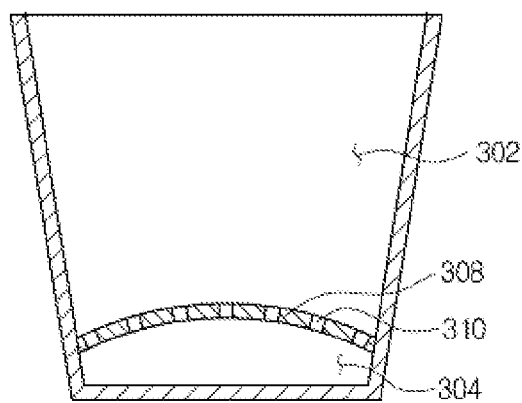
FIG. 4 is a cross-sectional view of the container shown in FIG. 2.

As shown in FIG. 4, the container 300 holds a dome-shaped dividing plate 308 with numerous holes. This plate 308 divides the interior space of the container 300 into an upper space 302 and a lower space 304, and blood discharged from the gauze 10 contained in the upper space 302 passes through the holes 310 and collects in the lower space 304. The reason for this division is because a marker 12 located in or near collected blood may not be recognized due to inadequate contrast between the markers and blood (i.e. x-ray attenuation between the two materials may not be grossly different enough), resulting in an inaccurate count.

The marker 12 consists of a radiopaque material such as stainless steel, barium or thermoplastic resin, and is formed into a spherical shape. The marker 12 is fixed between two sheets of adhesive cloth or sewn into place. The cloth 14 containing the marker 12 is affixed to the gauze 10 by sewing or other similar means. It is preferable that the cloth 14 has a thickness greater than half of the diameter of the marker, such that the distance between the markers 12 in the container 300 will be greater than diameter of the marker, and therefore make it possible to accurately count the markers by avoiding overlap.

The tray 320 functions to support the container 300. Relative movement occurs between the tray 320 and the radiographic unit; for example, if the tray 320 is fixed, the radiographic unit is configured to be moved, and if the radiographic unit is fixed, the tray 320 is configured to be moved. The relative movement includes rotational movement, linear movement, and curved movement having a specific trajectory.

As an example of the relative movement between the tray 320 and the radiographic unit, if the tray 320 is rotated, it is rotated utilizing a driving gear (not shown) and a driving motor (not shown).

The function of the radiographic unit is to radiograph the contents of the container 300 in variable angles using X-ray and includes an arm 408, a mounting arm 406, a tray-moving mechanism (338), an X-ray tube 402, and a detector 404.

The arm 408 is coupled to the outer circumferential surface of the supporting pillar 330. In instances where the tray 320 is rotated as described above, the arm 408 is fixedly coupled to the supporting pillar 330. In instances where the tray 320 is fixed and the radiographic unit is rotated, the arm 408 is rotatably coupled to the supporting pillar 330. In this case, the arm 408 is rotated by separate rotating means (not shown).

The installing part 406 is fixed to one end of the arm 408, and the X-ray tube 402 is fixed to the upper end of the installing part 406. The detector 404 is fixed to the other end of the arm 408 so as to detect X-rays irradiated from the X-ray tube 402 and passed through the container 300, then transfer the detected information to the controller 700.

The controller 700 controls the technical parameters of the unit, which includes the movement speed of the tray 320, exposure time, energy level and tube current (amperage) of X-ray tube. The controller 700 operates the X-ray tube 402, movement of the tray 320 and movement of the arm 408, depending on the methods of obtaining radiographic images.

In the above embodiment, radiographs are obtained at various angles by the movement of the tray 320 or the radiographic unit relative to each other. The radiographic unit can include multiple X-ray tubes 402 and detectors 404, although this is not indicated in the diagram.

The controller 700 receives radiograph information from the detector 404, counts the total number of markers 12 in the container 300 using this information, and then transfers the count information to the display 204. If the markers 12 have varying diameters, they 12 are grouped according to diameter. Further, the controller 700 compares the number of used gauzes 12 with the number of the gauzes input by the user into the display 204, determines if the numbers match, then transfers the results to the display 204. If the markers 12 have various diameters, the controller 700 determines whether the numbers are in agreement with each other according to diameter, then transfers the result of the determination to the display 204.

In the projected radiographs obtained as described above, multiple markers in the container may be superimposed and therefore appear as one marker. In order to prevent counting errors caused by this superimposition, the controller (700) can perform a tomographic reconstruction using multiple radiographs taken at various angles to obtain X-ray attenuation coefficients at each point in the pre-specified three-dimensional (3-D) space, thereby allowing separation of the superimposed markers in three dimensions and producing a reliable count.

The tomographic reconstruction process uses the same principle of the CT (computed tomography) system used in medical imaging and non-destructive testing applications. The reconstruction is based on the modeling of the X-ray projection process as a mathematical integration of X-ray attenuation coefficients of the materials within the 3-D space, which includes the container along the transmission line of X-ray as shown in equation (1).

$$I_d(y) = I_0 \exp(-\int \mu(x,y) dx) \qquad \text{equation (1)}$$

Figures 5, 6:
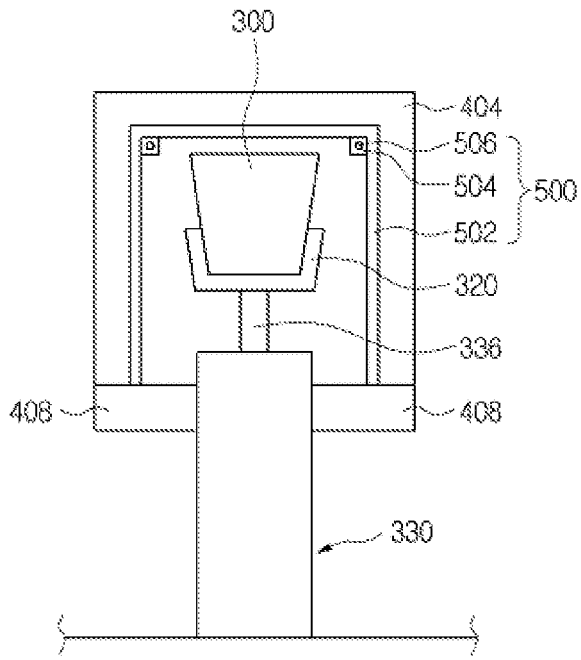
FIG. 5 is the calibration device, located outside of the container, as viewed from the x-ray tube.
FIG. 6 is schematic drawing of the tomographic reconstruction method using radiographed data obtained at various angles.

Based on this modeling, the attenuation coefficients of the materials at each point in the 3-D space can be obtained by solving the simultaneous mathematical equations for each pixel of the projected X-ray images taken at various angles as shown in FIG. 6.

In this tomographically reconstructed image, the superimposed markers in the projection radiographs can be easily separated and recognized by computer algorithm because the tomographic image data provides 3-D information of the x-ray attenuation properties, which are not available in the projection radiographs.

Using the attenuation coefficients, the controller 700 can separate the pixels of the marker from other pixels using the reference attenuation value of the known marker material. In one representation, the controller compares the attenuation value of each pixel in the 3-D tomographic image data with the reference attenuation value of the marker material and selects only those pixels having differences within an acceptable range, thereby separating those pixels belonging to the marker from those belonging to sponges and other materials.

The controller 700 may further segment the separated pixels of individual objects by applying the region growing technique to group neighboring pixels having similar attenuation values together.

Region growing is a technique used to segment groups of neighboring pixels with similar values by first choosing a seed pixel, then comparing it with the pixel values of neighboring pixels. Those pixels having differences of less than a predefined tolerance range in pixel value from that of the seed pixel are placed into the same group, and each newly-added pixel is set as the seed pixel for the next iteration to continue the growing of the segmented region, such that all of the connected pixels having similar values are eventually segmented out from the dissimilar pixels.

Note that the controller 700 may remove non-marker objects from the list of candidate objects to be counted in order to improve the accuracy of marker counting.

It is noted that the sponge may contain non-marker, solid objects, such as metallic clips or bone fragments, which have high attenuation coefficients similar to that of the marker material. As a means to removing these non-marker solid objects, the controller 700 may use the known shape of the marker and the uniformity of the attenuation coefficient within the marker. For example, the controller may examine the sphericalness and attenuation coefficient uniformity of each segmented object.

The sphericalness of an object may be calculated by utilizing the relationship of the volume V and effective radius R of an object, as described in equation (2). The sphericalness of an object is closer to 1 when its shape is closer to that of a sphere and closer to 0 when its shape is less spherical.

$$K = V \times 3/(4\pi R^3) \quad \text{equation (2)}$$

The segmented objects can be classified as spherical shapes or non-spherical shapes by applying the appropriate threshold to the sphericalness value obtained using equation (2).

Thus, non-marker solid objects having a non-spherical shape can be removed from the candidate object field by examining the sphericalness of the objects, since only markers of spherical shape are used for the gauze. The attenuation coefficient uniformity test uses the statistical properties of the attenuation coefficients of pixels within each segmented object, which allows distinction of metallic markers from sphere-shaped bone fragments that have passed the sphericalness test. This is because the marker material, e.g. iron, has a uniform attenuation coefficient, whereas the bone fragments typically have non-uniform attenuation coefficients. Mean and standard deviation may be used as statistical descriptors to measure the uniformity of attenuation coefficient within the segmented object.

Moreover, in case where multiple types of sponges are used, the controller 700 may classify the segmented objects into different types and count the number of sponges according to type.

In such cases, the controller 700 may compare the size of each segmented object to the previously determined sizes of reference markers to classify the object by type. This is done by determining for which type the size error lies within a previously defined tolerance range.

With those segmented objects that have passed the non-marker testing and marker type classification, the controller 700 then counts the number of markers in each type and concludes the counting procedure.

The calibration unit 500 checks whether the container 300 is projected within the predetermined position of the detector and whether the image quality is acceptable for the counting. As shown in FIG. 5, the calibration unit 500 includes a frame 502, background material 504, and a calibration marker 506.

The frame 502 is located around the container 300 but does not rotate with the tray when object rotation method is used to obtain images at various angles. The background material 504 is fixed to the frame 502 and is composed of material with an X-ray attenuation similar to that of blood soaked gauze. The calibration marker 506 is fixed to the center of the background material 504 and is composed of material with the same X-ray attenuation as that of the marker 12. The size of the frame 502 is set so that the calibration markers 504 can be located outside of the container in all images.

In cases where the present gauze counting device 100 includes the calibration unit 500 as described above, the controller 700 calculates a contrast ratio between the background material 504 and the calibration marker 506, and then halts subsequent processes if the contrast ratio is less than a predetermined value. Further, if any part of the calibration marker 506 is not included in the image, the controller 700 halts the subsequent processes. After stopping the process, the controller 700 relays a warning message to the display 204.

The user inputs the start and end commands into the display 204, which then relays the command to the controller 700. The display 204 also receives and displays patient information, along with the number of gauzes estimated to be placed into the container 300. If numerous types of gauze are used, the display 204 exhibits the gauze counts according to the type of gauze. Furthermore, the display 204 shows the number of markers 12 calculated by the controller 700 according to marker size, indicating whether the number of the markers 12 calculated by the controller 700 corresponds with the number of the gauzes input by the user in each category of marker size (type of gauze (10)) and also displays a warning message, which is transferred from the controller 700.

The present gauze counting device 100 can be operated by commercial electric power, but includes a separate generator 600 for mobility of the cabinet 200 in case of emergency. In such case, the generator 600 supplies power to the radiographic unit, the controller 700, and the display 204, and produces the power to obtain radiographs of the container 300 at various angles.

The operation of the gauze counting medical device 100 is described as follows.

First, the user installs the container 300, including the gauze 10 on the tray 320, and then inputs the starting command and the number of gauzes 10 estimated to be placed in the container 300.

Next, the X-ray is applied in accordance with the predetermined angles and the predetermined number of exposures. The transmitted X-ray is received by the detector 404, and the information is then transferred to the controller 700. The controller 700 calculates the number of markers 12 included in the container 300 using the detected information and determines whether the calculated number of markers 12 corresponds with the number of the gauzes input by the user. The display 204 shows the number of the gauzes input by the user, the number of markers 12 calculated by the controller 600, and whether the numbers correspond with each other.

The following is a description of the method for the automatic counting of medical gauzes according to the present invention.

This method includes four steps.

In step one, radiographs of the container 300 holding the gauze 10 with the radiopaque markers 12 are obtained at various angles using X-ray. This first step is broken down into two parts: 1-1 and 1-2. In step 1-1, the container 300 is exposed to the X-ray, and in step 1-2, the X-ray passing through the container 300 is detected. In both steps 1-1 and 1-2, X-ray exposure and detection are performed at multiple points along the circumference of the container 300 in order to radiograph the container 300 at various angles. Alternatively, X-ray exposure and detection may be simultaneously performed at multiple points along the circumference of the container 300. The exposure angle of the X-ray and the number of X-ray exposures may be set according to the number of gauzes 10 placed in the container 300, the size of the marker, the resolution of the image, and other factors.

Figure 7:
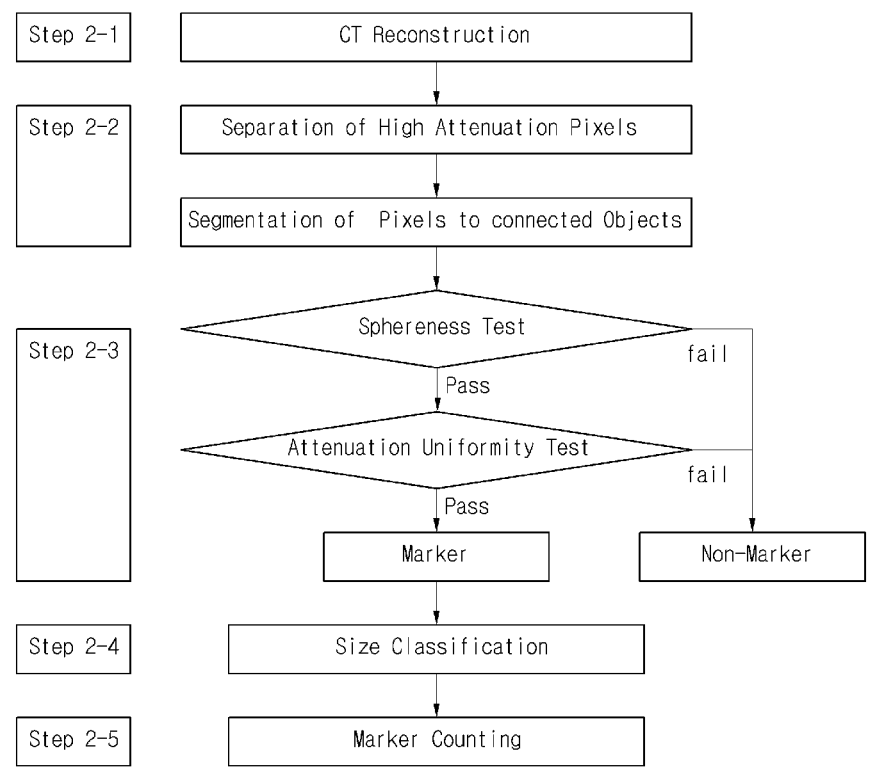
FIG. 7 is flow chart of the automatic counting of medical gauze.

In the second step, the total number of markers in the container 300 is calculated using radiographic information from the first step. This second step includes steps 2-1 to 2-5, as illustrated in FIG. 7.

In step 2-1, the controller 700 performs a tomographic reconstruction using the radiographs obtained at various angles. Because three-dimensional data of attenuation coefficients are provided at each point within the container by tomographic reconstruction and the space between markers are secured by using wrapping cloth thicker than half of the diameter of the marker, any markers superimposed in the projection radiographs can be easily distinguished and separated in the tomographically reconstructed image data.

In step 2-1, the pixels with high attenuation coefficients in the tomographic image data are separated and segmented into individual connected objects. Because the attenuation coefficient of the markers is much higher than other materials within the container, the marker pixels can be easily separated from the rest by applying the appropriate threshold. The high attenuation components of the tomographic image data are segmented into individual connected objects by applying the region growing technique.

In step 2-3, non-marker objects are removed from the list of segmented objects, obtained as described above. The sponge may contain various non-marker solid objects, such as metallic clips or bone fragments, which become embedded during the operational procedure. To remove these non-marker objects, the controller examines the uniformity of attenuation coefficients and sphericalness of each segmented object.

In step 2-4, the remaining segmented objects are classified into different types by comparing the measured size of each segmented object with previously determined sizes of reference markers.

In step 2-5, the controller 700 counts the number of classified objects for each type, determines the total, and concludes the counting procedure.

Moreover, in the second step, the total calculated number of gauzes is compared with the number of the gauzes input by the user. In the third step, the number of the markers calculated in the second step is displayed visually. Patient information and the number of the gauzes 10 estimated to be placed in the container 300 are also displayed in this step. If various types of gauze are used, the totals are displayed according to gauze type. Additionally, the number of the markers 12 can be displayed according to size, along with whether the number of the markers 12 calculated in the second step corresponds with the estimated number of gauzes 10.

The fourth step is performed before the first step or during the first and second steps, and includes steps 4-1 to 4-3.

In step 4-1, a set of background materials 504, which are provided around the container 300 and have an X-ray attenuation similar to that of blood, and calibration markers 506, which are respectively fixed to a center portion of each background material 504 and have the same X-ray attenuation as that of the marker, are radiographed using X-ray. It is then determined whether the calibration markers are included in the image and whether the contrast ratio between the background material 504 and the calibration markers 506 is less than a predetermined value. If at least one of the calibration markers is not included in the radiographed image, or if the contrast ratio between the background material 504 and the calibration markers 506 is less than the predetermined value, the subsequent processes are halted. In this case, a warning message may be generated and transferred.

What is claimed is:

1. A device for counting medical gauze automatically, comprising:
    a container to collect gauze embedded with radiopaque markers;
    a support, which supports the container;
    a radiographic unit, which radiographs the container at various angles using X-ray;
    a controller, which receives information from the radiographic unit and counts the total number of markers in the container using such radiographic information; and
    a display, which controls the unit and displays the number of the markers calculated by the controller, wherein the controller calculates the X-ray attenuation coefficients at every position within the pre-specified three-dimensional (3-D) space encompassing the container by performing a tomographic reconstruction using the radiographs taken at various angles, thus preventing errors in gauze counting potentially caused by superimposed markers in the projection X-ray images.

2. The device of claim 1, wherein the container comprises a dome-shaped plate dividing the internal space of the container into an upper and a lower space, and such dividing plate contains numerous holes through which blood absorbed by the gauze drains from the upper space into the lower space.

3. The device of claim 1, further comprising mechanical means of moving the support such that the supported container is moved relative to the detector and x-ray tube.

4. The device of claim 1, wherein a calibration unit is fixed to the radiographic unit, and
    the calibration unit comprises:
    a frame, which is fixed to the radiographic unit to enclose the container;
    a background material, which is fixed to the frame and has an X-ray transmittance similar to that of blood; and
    a calibration marker, which is fixed to a center portion of the background material and has the same X-ray transmittance as that of the radiopaque marker.

5. The device of claim 4, wherein the controller calculates the contrast ratio between the background material and the calibration marker and stops the subsequent processes if the calibration marker is not included in an image or the contrast ratio is less than the predetermined value.

6. The device of claim 1, wherein the controller compares the calculated number of gauzes with the number of gauzes input by the user, then determines whether the numbers are in agreement with each other.

7. The device of claim 1, wherein the marker is fixed in cloth that is affixed to the gauze and formed into a spherical shape, and the cloth has a thickness of 1 mm or more.

8. The device of claim 1, wherein the radiographic unit comprises:
    multiple arms, which are coupled to a supporting pillar buttressing the support;

multiple installing parts, which are each fixed to one end of the numerous arms;

multiple X-ray tubes, each of which are fixed to the end of an installing part so as to irradiate X-ray to the container; and multiple detectors, each of which are fixed to the opposite ends of the numerous arms so as to detect the X-ray passing through the container, then transfer the detected information to the controller.

9. The device of claim 1, wherein if markers of varying sizes are combined in the container, the controller calculates the number of markers according to the sizes thereof, and the display indicates the number of markers according to size.

10. The device of claim 1, wherein the controller separates the image pixels of tomographically reconstructed image data of markers from those of other materials by comparing the X-ray attenuation coefficients of each pixel to the known attenuation coefficient of the reference marker material, thereby selecting those pixels with attenuation coefficients falling within the accepted range of standard deviation, and further segments those separated image pixels to the individual spatially connected objects.

11. The device of claim 10, wherein the controller removes other object pixels from the list of candidate objects to be counted by examining the sphericalness of the object and uniformity of attenuation coefficients within the object.

12. The device of claim 10, wherein the controller categorizes the objects into different marker types by comparing the measured size of each segmented object with previously determined sizes of reference marker types.

13. A method for counting medical gauze automatically, comprising:

radiographing the container, which collects the gauze embedded with radiopaque markers, using X-ray;

calculating the number of markers in the container using information obtained from radiographing the container; and displaying the calculated number of markers, wherein the calculation of the number of markers in the container comprises:

performing a tomographic reconstruction of a plurality of radiographs taken at various angles to calculate X-ray attenuation coefficients at each point within a pre-specified three-dimensional (3-D) space encompassing the container;

separating the pixels of the tomographically reconstructed image data of the marker from those of gauzes and other materials by comparing the X-ray attenuation coefficients of each pixel to the known attenuation coefficient of the reference marker material, and further segmenting those separated image pixels into individual spatially connected objects;

classifying the segmented objects in the reconstructed tomographic images into different marker types by comparing the measured size of each segmented object with the previously determined sizes of reference marker types; and counting the classified markers for each type.

14. The method of claim 13, wherein the radiographing of the container comprises:

irradiating the container with X-ray; and detecting the X-ray passed through the container, wherein the irradiation and X-ray detection are performed multiple times sequentially.

15. The method of claim 13, wherein the radiographing of the container comprises:

irradiating the container with X-ray; and detecting the X-ray passed through the container, wherein the irradiation and X-ray detection are performed multiple times simultaneously.

16. The method of claim 13, further comprising a calibration process before or during the radiographing of the container and the calculation of the number of the markers in the container, wherein the calibration process comprises:

obtaining radiographic images of the container and the calibration unit, located outside of the container but within the projected field of the detector(s), testing if the calibration unit is included in all images and testing if the calibration markers and background materials have the same x-ray attenuation characteristics as the radiopaque markers and blood soaked surgical gauzes, respectively, which is necessary for the controller to determine whether the radiographic unit and container are in correct alignment and to determine whether exposure of x-ray tube is adequate for the next step of the calculation process;

determining whether the calibration markers are included in the radiographed image and whether the contrast ratio between the background material and the calibration markers is less than a predetermined value; and halting subsequent processes if any of the calibration markers are not included in the radiographed image, or if the contrast ratio between the background material and the calibration markers is less than the predetermined value.

17. The method of claim 13, wherein calculating the number of the markers in the container, the number of gauzes input by the user is compared with the number of markers, and it is then determined whether the numbers are in agreement with each other; and in displaying the total calculated number of markers, such display includes the number of gauzes input by the user, the number of markers, and whether both numbers are in agreement with each other.

18. The method of claim 13, wherein if markers of different sizes are combined in the container, the number of markers is calculated and totals are displayed according to marker size.

19. The method of claim 13, wherein the objects consisting of non-marker solid materials with high attenuation coefficients are removed from the list of candidate markers to be counted by examining the sphericalness of the object and uniformity of attenuation coefficients within the object.

* * * * *